United States Patent
Reich et al.

(10) Patent No.: US 10,213,103 B2
(45) Date of Patent: Feb. 26, 2019

(54) TOPOGRAPHY MODULE FOR OPHTHALMOLOGICAL DEVICES WITH A DISTANCE-INDEPENDENT KERATOMETER AND METHOD FOR THE USE THEREOF

(71) Applicant: Carl Zeiss Meditec AG, Jena (DE)

(72) Inventors: Matthias Reich, Jena (DE); Rico Fuchs, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 121 days.

(21) Appl. No.: 15/315,319

(22) PCT Filed: Jun. 4, 2015

(86) PCT No.: PCT/EP2015/062494
§ 371 (c)(1),
(2) Date: Nov. 30, 2016

(87) PCT Pub. No.: WO2015/185682
PCT Pub. Date: Dec. 10, 2015

(65) Prior Publication Data
US 2017/0188821 A1  Jul. 6, 2017

(30) Foreign Application Priority Data

Jun. 5, 2014 (DE) .................. 10 2014 210 786

(51) Int. Cl.
*A61B 3/107* (2006.01)
*A61B 3/103* (2006.01)
(Continued)

(52) U.S. Cl.
CPC ............ *A61B 3/107* (2013.01); *A61B 3/1005* (2013.01); *A61B 3/1035* (2013.01); *A61B 8/10* (2013.01);
(Continued)

(58) Field of Classification Search
CPC .......... A61B 3/0025; A61B 3/102; A61B 3/14; A61B 3/12; A61B 3/0008; A61B 3/1005;
(Continued)

(56) References Cited

U.S. PATENT DOCUMENTS

| | | |
|---|---|---|
| 4,660,946 A | 4/1987 | Nakamura et al. |
| 4,685,140 A | 8/1987 | Mount, II |

(Continued)

FOREIGN PATENT DOCUMENTS

| | | |
|---|---|---|
| DE | 699 32 208 T2 | 5/2007 |
| DE | 10 2012 019 474 A1 | 4/2014 |

(Continued)

OTHER PUBLICATIONS

English translation of PCT International Preliminary Report on Patentability for International Application No. PCT/EP2015/062494, dated Dec. 15, 2016, 14pages.

(Continued)

*Primary Examiner* — Hung Dang
(74) *Attorney, Agent, or Firm* — Patterson Thuente Pedersen, P.A.

(57) ABSTRACT

A module for ophthalmological devices which enables ophthalmological devices to carry out keratometry and topography measurements of the eye. The proposed topography module is provided for ophthalmological devices with a distance-independent keratometer. The topography module, which is used to generate the luminous pattern, is arranged in a fixed or moveable manner in the beam path between the ophthalmological device and the eye. A control unit is provided to control the topography module for generating luminous patterns. The provided evaluation unit is also suitable to carry out keratometric as well as topographic evaluations of the reflection images of an eye, captured and transmitted by the detection unit. The invention enables (Continued)

ophthalmological devices, which are equipped with a distance-independent keratometer, to carry out additional topographical measurements on the eye.

19 Claims, 4 Drawing Sheets

(51) Int. Cl.
*A61B 8/10* (2006.01)
*G01B 11/25* (2006.01)
*A61B 3/10* (2006.01)
*A61F 9/008* (2006.01)

(52) U.S. Cl.
CPC ............ *G01B 11/2513* (2013.01); *A61B 3/10* (2013.01); *A61F 2009/00882* (2013.01)

(58) Field of Classification Search
CPC .... A61B 3/13; A61B 2090/3735; A61B 3/107
USPC ................................ 351/212, 206, 221, 246
See application file for complete search history.

(56) References Cited

U.S. PATENT DOCUMENTS

| | | |
|---|---|---|
| 5,110,200 A | 5/1992 | Snook |
| 5,194,882 A | 3/1993 | Penney |
| 5,684,562 A | 11/1997 | Fujieda |
| 5,864,383 A | 1/1999 | Turner et al. |
| 6,048,065 A | 4/2000 | Davis et al. |
| 6,070,981 A | 6/2000 | Mihashi et al. |
| 6,116,738 A | 9/2000 | Rorabaugh |
| 6,575,573 B2 | 6/2003 | Lai et al. |
| 6,692,126 B1 | 2/2004 | Xie et al. |
| 6,779,891 B1 | 8/2004 | Barth et al. |
| 7,976,163 B2 * | 7/2011 | Campbell ............... A61B 3/107 351/212 |
| 9,084,564 B2 | 6/2015 | Bublitz et al. |
| 9,375,140 B2 | 6/2016 | Breitenstein et al. |
| 2009/0161090 A1 | 6/2009 | Campbell et al. |
| 2009/0268020 A1 | 10/2009 | Buckland et al. |
| 2012/0265181 A1 | 10/2012 | Frey |
| 2014/0104574 A1 | 4/2014 | Grenon et al. |

FOREIGN PATENT DOCUMENTS

| | | |
|---|---|---|
| EP | 0 983 757 A2 | 3/2000 |
| EP | 2 583 620 A2 | 4/2013 |
| WO | WO 00/33729 | 6/2000 |
| WO | WO 2012/160049 A1 | 11/2012 |
| WO | WO 2014/049124 A1 | 4/2014 |

OTHER PUBLICATIONS

International Search Report with English translation for corresponding International Application No. PCT/EP2015/062494 dated Nov. 25, 2015; 7 pages.

Written Opinion for corresponding International Application No. PCT/EP2015/062494 dated Nov. 25, 2015; 7 pages.

Search Report for corresponding German Application No. 10 2014 210 786.5 dated Mar. 10, 2015; 8 pages.

* cited by examiner

TOPOGRAPHY MODULE FOR OPHTHALMOLOGICAL DEVICES WITH A DISTANCE-INDEPENDENT KERATOMETER AND METHOD FOR THE USE THEREOF

RELATED APPLICATIONS

This application is a National Phase entry of PCT Application No. PCT/EP2015/062494 filed Jun. 4, 2015 which application claims the benefit of priority to German Application No. 10 2014 210 786.5, filed Jun. 5, 2014, the entire disclosures of which are incorporated herein by reference.

FIELD OF THE INVENTION

The present invention relates to a module for ophthalmological devices provided for distance-independent keratometry measurements. By application of this module, the ophthalmological devices are then capable of implementing topographic measurements of the eye, in addition to keratometric measurements.

BACKGROUND

While keratometry is understood to be the measurement of the curvature of the cornea, topography relates to the three-dimensional measurement of geometric surfaces, in our case of the cornea of an eye.

The measurement of cornea curvature normally occurs in that the cornea is illuminated in a structured manner, and the light beams reflected by the cornea are detected. According to the prior art, two different optical approaches are known for this.

In the first, more traditional approach, the cornea is illuminated with structures, e.g. individual light structures or Placido ring systems, and the resulting images are viewed with conventional optical imaging systems. Because of the type of lighting, in order to obtain a precise evaluation of the reflected images it is absolutely necessary to determine the distance between the eye or cornea and the measurement device. Appropriate assemblies for this shall be explained in brief below.

With the method known for some time, and used substantially in so-called keratometers or keratographs, individual light structures or Placido rings are imaged reflection from the precorneal tear film, and the reflected signals are observed with imaging optics or recorded with a camera and evaluated. Depending on the curvature of the cornea, the pattern that is reflected and detected by the camera is scaled in size. In order to obtain a determination of the curvature from these reflection signals, the size of the reflected pattern must be compared with a known shape, normally resulting in a sphere having a radius of 7.8 mm. A solution of this type is described, for example, in U.S. Pat. No. 4,684,140 A.

The Placido disks used in topographs for generating concentric rings are not necessarily a planar disk. Although such planar Placido disks are sufficiently known in the prior art, and described, for example, in U.S. Pat. Nos. 5,110,200 A and 5,194,882 A, funnel-shaped (U.S. Pat. Nos. 5,684,562 A, 6,116,738 A) or spherically curved (U.S. Pat. No. 5,864,383 A) Placido disks, are more commonly used.

Solutions for ophthalmometers (also keratometers) are described in U.S. Pat. Nos. 6,575,573 B2 and 6,692,126 B1, which are supplemented by slit lamp projectors. While the imaging of Placido ring systems is provided for the measuring of the surface curvature of the cornea of the eye, sectional images of the eye are generated with the slit lamp projectors, from which the thickness of the cornea of the eye can be determined. As a result of this combination, a cornea thickness profile can be determined.

One disadvantage of these types of solutions can be seen in that the precision of the measurement is strongly dependent on the angular relationships, and thus on the measurement distance. Very different methods are used to determine, or check for, the correct measurement distance. As such, the measurement can be automatically triggered when the correct working distance has been reached. On one hand, this can occur through a correction of the erroneous distance prior to each measurement, in that the distance, or the position, is determined and, if necessary, corrected, using photo sensors, contacts or additional measurement systems.

By way of example, U.S. Pat. Nos. 6,048,065 A and 6,070,981 A are specified in this regard. The solutions described therein depict topographs based on a Placido disk. For checking for the correct measurement distance, both solutions make use of a point light source, the light from which illuminates the cornea, is reflected therefrom, and reproduced on a CCD camera as a point image. The position of the point image inside the recording range provides information regarding the distance between the Placido disk and the eye. For an exact positioning, the Placido disk is displaced until the distance is optimized. The measurement first begins at this point.

The distance-independent approach enables the projection of numerous points, circles or other suitable patterns with limited technical expenditure. Although a detailed determination of the topography of the cornea is substantially simplified by this, it is disadvantageous thereby, that a relatively complex measurement system for determining the distance to the eye is necessary.

There are approaches that combine established keratometers with a topography measurement device for measuring the cornea. For this, in addition to the existing ring structure, 6 light points are integrated on the Placido disk, for example. The disadvantage with these types of solutions, however, is that the projection of the 6 light points does not occur in the form of parallel beams, i.e. in a distance-independent manner, and for this reason, an additional distance measurement device is needed.

As such, an ophthalmological device in the form of a 2-zone keratometer is known, with which additional topography measurements can be carried out through an attachment. The attachment has the form thereby of a (funnel-shaped) Placido disk. Because the projection of the measurement points likewise does not occur in a distance-independent manner thereby, the implementation of a distance measurement system is needed.

In the second approach, the structures are projected onto the cornea from the infinite, thus in the form of parallel beams, and the image reflected from the cornea is observed with a telecentric lens assembly. Because of the projection of parallel beams, this approach is distance-independent, such that the determination of the distance between the eye and the measurement device is unnecessary.

In addition, there is an approach described in WO2000/33729 A2, in which 6 punctiform structures are projected onto the cornea from the infinite using 6 separate lenses.

U.S. Pat. No. 4,660,946 A describes a solution for measuring the shape of the cornea based on a disk-shaped Fresnel cylindrical lens. Each ring of the Fresnel cylindrical lens is annularly illuminated individually by application of annular cylindrical lenses. On one hand, the number of implementable rings is limited by the disk-shaped structure, and on the other hand, it becomes increasingly difficult to implement this type of lighting as the number of rings increases.

Another solution is described in WO 2012/160049 A1. Therein, an element in the form of a Fresnel axicon lens is disposed in the beam path, and illuminated by a lighting unit over its entire surface with plane waves. Aside from in the region of the telecentric distance-independent image capturing, the Fresnel axicon has annular structures of different radii. Although this solution enables the generation of numerous parallel beams having different angles of incidence, very high demands, however, in terms of precision, are placed on its production as well as the adjustment thereof. Furthermore, this solution requires a great deal of space, making it difficult to integrate it in multifunctional ophthalmological devices.

SUMMARY

In evaluating the solutions known according to the prior art, it can be established that for the measurement of the cornea, in particular in conjunction with calculating an intraocular lens (IOL), the distance-independent approach exhibits significant advantages. However, only up to 6 individual points are detected due to the, in principle, high technical complexity inherent in the projection. As a result, detection of deviations from an ellipsoidal shape in the surface of the cornea is prevented, which may have a negative effect on the precision of an optimal IOL selection.

Example embodiments of the invention improve and expand on an ophthalmological device for distance-independent keratometry measurement, such that topographic measurements of the eye can also be implemented. In particular, example embodiments of the invention combine the advantages of the solutions from the prior art in the simplest possible manner, and require, thereby, very little technical expenditure. Furthermore, it is desirable when the solution that is to be developed is also suitable for existing ophthalmological devices, in particular 6 point keratometers.

This object shall be achieved by the topography module for ophthalmological devices, which have a distance-independent keratometry measurement device having a detection beam path and the necessary units for this, for illumination and detection, as well as control and evaluation, in that the topography module serves to generate luminous patterns, and is disposed in a stationary or moveable manner in the beam path between the ophthalmological device and the eye, in that the topography module transmits the keratometry beam, and has devices that ensure placement at a defined position in the beam path, in that the existing control unit is capable of appropriately controlling the topography module for the generation of light patterns, and in that the existing evaluation unit is suitable for evaluating, in both a keratometric as well as topographic manner, the reflected images of an eye recorded and transmitted by the detection unit.

With an example method according to the invention for keratometric and topographic measurement of the cornea of an eye using a topography module for ophthalmological devices, in which, for the keratometric measurement, the eye is illuminated and detected in a distance-independent manner, and in which the topography module is placed in the beam path in a first step, and integrated into the control and evaluation logarithm, this object is achieved by implementation of the following steps:

b) recording a second image, in which the fixation light and the lighting for the keratometric measurement are switched on, c) recording a second image, in which the fixation light and the lighting for the topographic measurement are switched on, e) evaluation of the recorded images and outputting the results.

According to example embodiments of the invention, it is possible for ophthalmological devices, which have a distance-independent keratometry measurement device, to implement additional topographic measurements of the eye. The solution thus unites the advantages of keratometric and topographic measurements of the eye with little technical expenditure.

Example embodiments of the invention are suitable, both as an alternative add-on module, and, with the appropriate adjustments, also as a retrofitting module for ophthalmological devices already in use. In particular, the proposed solution is suitable for use in distance-independent 6 point keratometers.

BRIEF DESCRIPTION OF THE DRAWINGS

The invention shall be explained in greater detail below, based on exemplary embodiments. Therein.

DETAILED DESCRIPTION

The topography module according to example embodiments of the invention is intended for ophthalmological devices, which have a distance-independent keratometry measurement device with a detection beam path and the necessary units for this, for illumination, detection, as well as control and evaluation.

In accordance with example embodiments of the invention, the topography module used for the generation of luminous patterns is disposed in a stationary or moveable manner in the beam path between the ophthalmological device and the eye, for which it has devices that ensure placement at a defined position in the beam path. The existing control unit is capable of controlling the topography module in order to generate the light patterns. Furthermore, the existing evaluation unit is suitable for evaluating the reflected images of an eye recorded and transmitted by the detection unit, both keratometrically as well as topographically.

The topography module has a disk-shaped, planar, partially conical, or similar shape.

Although for the topography module, a planar shape is preferred, at least in its center, it may have other geometries extending outward, such as a conical or similar shape, for example.

According to a first design, the topography module is transparent and is composed of, for example, glass or plastic.

In accordance with the invention, the topography module has local diffusing or reflecting inhomogeneities in its volume, or structures in or on its surface, or a luminous opto-electronic coating, for generating the light pattern necessary for the topography measurements. Typically, well known patterns, such as rings, grids, points, bars, etc. are used as the light pattern for topography measurement. Preferably, the sizes of the diffusing structures can be varied such that the generated patterns exhibit a uniform brightness or illumination level.

In accordance with a first example design, a lighting unit is disposed on the topography module for illuminating the local diffusing inhomogeneities in its volume, or the structures on its surface, such that the light is introduced laterally into its peripheral surface(s).

The light coupled via the peripheral surface(s) is conducted through total reflection over the entire disk cross section, and is diffused or decoupled at the inhomogeneities or structures, respectively, toward the eye.

Figure 1:
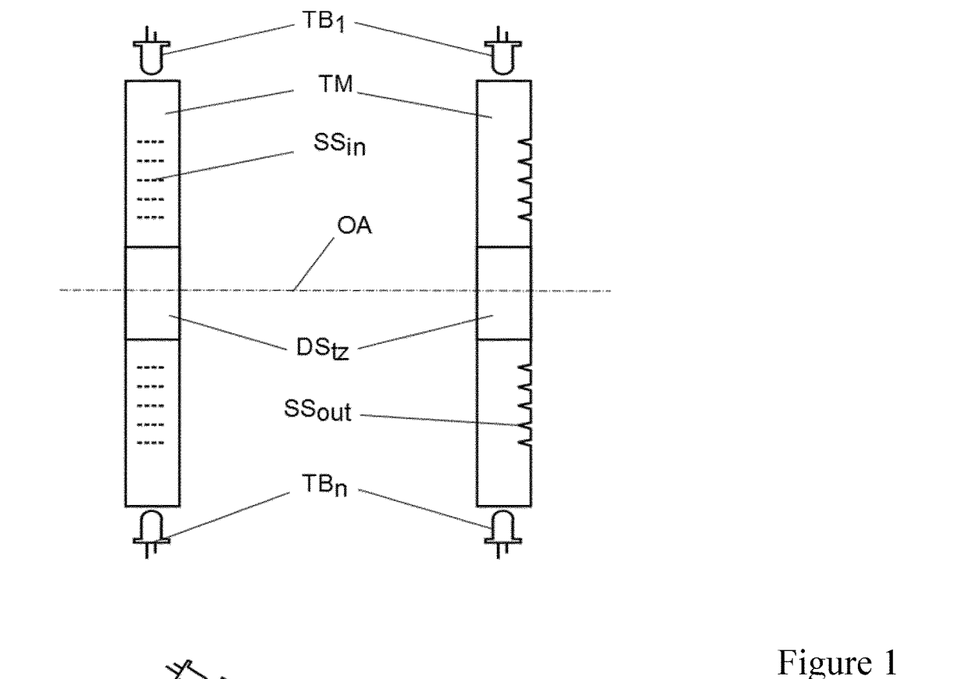
FIG. 1: depicts cross sections of disk-shaped, planar topography modules.

For this, FIG. 1 shows disk-shaped, planar topography modules in a cross section. While the topography module TM on the left-hand side has local diffusing inhomogeneities $SS_{in}$ in the interior of the disk volume, the topography module TM illustrated on the right-hand side has structures on its surface $SS_{out}$. A number n of topography light sources $TB_n$ are disposed on the topography module TM for lighting the internal or external diffusing structures $SS_{in}$ or $SS_{out}$, which represent the lighting unit as a whole. The light of the topography light sources $TB_n$ is introduced into the end surface of the topography module TM. The topography module TM for example has no diffusing structures surrounding the optical axis OA in the central region, because this region forms the telecentric detection beam path $DS_{tc}$.

Figure 2:
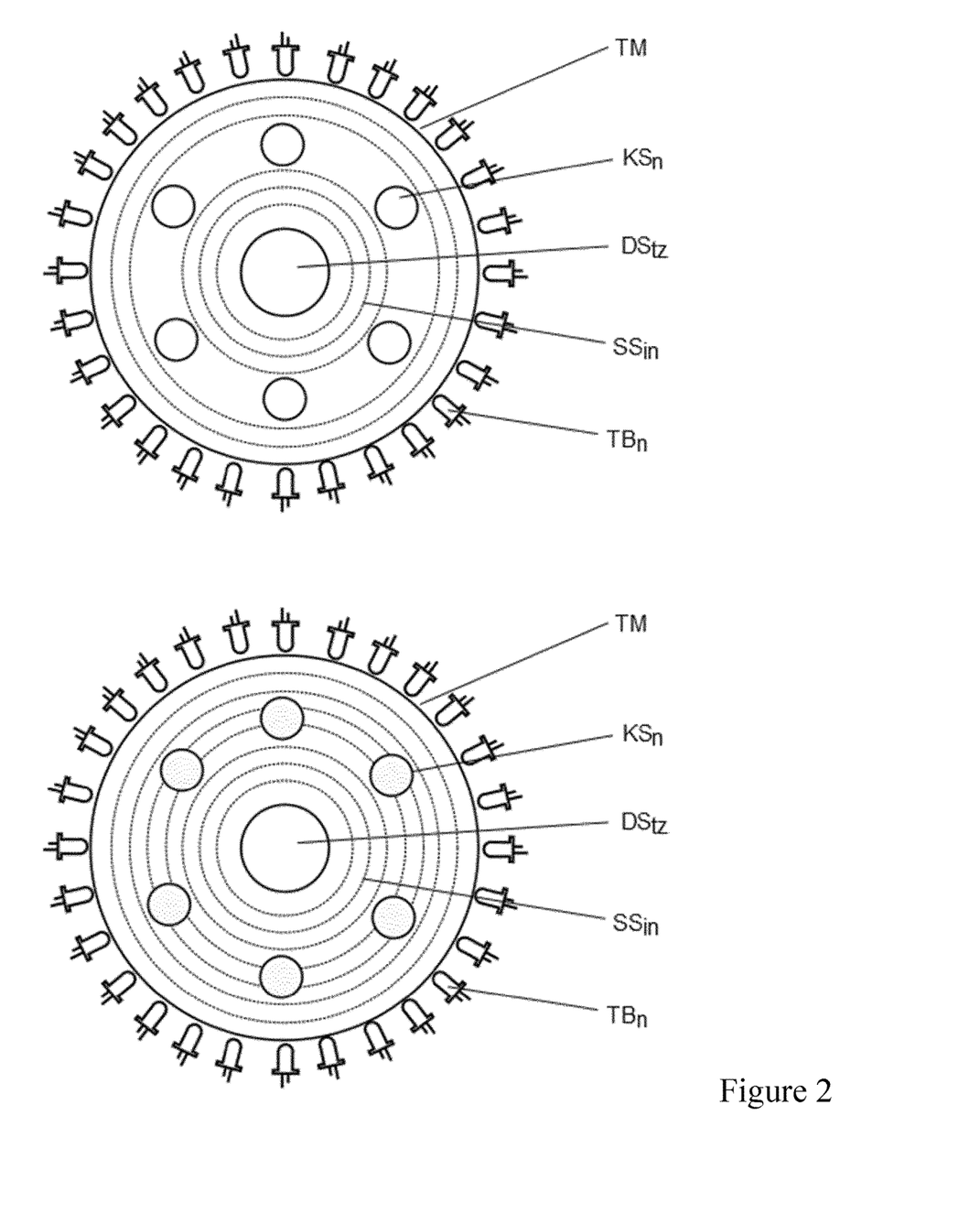
FIG. 2: depicts the front views of two topography modules.

As can be seen in FIG. 2, the lighting unit is composed of numerous lighting elements distributed over the circumference, for example in the form of light emitting diodes. The topography module does not necessarily have to have a rotationally symmetrical shape thereby.

Furthermore, the local diffusing inhomogeneities in its volume, or the structures on its surface are disposed such that both the beams of the keratometer light sources as well as the telecentric detection beam path are not affected, or only to a slight extent.

For this, FIG. 2 shows the front view of two topography modules TM with topography light sources TB distributed over the circumference thereof. The central region of the topography module TM is designed as an opening, or at least has no diffusing structures. As a result, it is ensured that the telecentric detection beam path $DS_{tc}$ is not affected by the local diffusing inhomogeneities $SS_{in}$. By way of example, structures are shown here, which generate light patterns in the form of a ring system that is similar to that of a Placido disk. The effect on the beam paths for the keratometer light sources $KB_n$ can be prevented in different ways.

The surface of the topography module TM in the upper drawing is divided from the inside toward the outside, such that following the telecentric detection beam path $DS_{tc}$, there is a first region, which contains local diffusing inhomogeneities $SS_{in}$ for generating the light pattern for the topography measurement, a second region, provided for the keratometer light sources $KB_n$, and a third region, which again contains local diffusing inhomogeneities $SS_{in}$ for generating the light pattern for the topography measurement.

In contrast thereto, with the topography module TM in the lower drawing, the local diffusing inhomogeneities $SS_{in}$ are simply interrupted at the locations of the beam path for the keratometer light sources $KB_n$. This may be necessary, in particular with an increasing density of the inhomogeneities $SS_{in}$.

In accordance with a second design, the topography module has an opto-electronic coating, with which the light pattern needed for the topography measurements is generated. Preferably, transparent OLED films are used thereby for the coating.

By application of an appropriate electrical activation, the OLED film is capable of depicting luminous patterns, such that no additional lighting unit is needed. Arbitrary, static and dynamic light patterns can be depicted thereby, depending on the type and manner of activation, which can be varied in terms of color and contrast.

Thus, the spacing and dimensions of the light structures can be adjusted in a variable manner. Each possible pattern structure can thus be generated: annular, punctiform, reticulate, or a combination thereof. The light pattern can for example be adapted to the anatomy as well as to the surface function that is to be optimized. A temporal adaptation of the structure formed during the measurement is also possible thereby. In this manner, the lighting structure can be adapted in an optimal manner to the individual anatomy of the eye that is to be measured. This is important for patients, in particular, whose corneas have scar tissue resulting from operations or accidents, which lead to strong distortions of the pattern projected onto the eye.

This is because it is important, for the measurement of reflected patterns for determining the topography of an eye, that the respective light source can be assigned distinctly to each measurement point. This is difficult in particular with deformed, pathological anatomies, because an overlapping or "overtaking" of the image points may occur. In this context, OLED films furthermore offer the advantage that light structures can be generated, which can be varied in terms of the color, contrast or sequencing thereof. As a result, the measurement points can also be distinctly assigned to the relevant light sources in the case of strong distortions. With the use of OLED films of this type, there is also the possibility of being able to depict additional light points for fixation with the topography module, in addition to the light patterns necessary for the topography measurement.

Another advantage can be seen in the flexibility of the OLED films. As a result, it is possible to realize non-planar geometries as well, in order to make optimal use of the available space in an ophthalmological device.

A possible source of interference signals in the construction described above is diffused light, which is emitted from the topography disk toward the device. This light illuminates the surface of the device, and thus reduces the contrast between the diffusion structures and the background in the image.

In accordance with an additional design aspect, the affect of this diffusion beam can be minimized through various approaches:
 in which the device housing located behind the topography module has a dark and/or matte surface,
 in which the diffusion structure is not located directly in front of the housing, and
 in which the topography module has appropriate coatings and/or coverings.

The regions of the beam paths of the keratometer light sources as well as the telecentric detection beam path are, thereby, excluded from the coating. Optical openings that cannot reflect light already exist in ophthalmological devices.

If different wavelengths are used for the keratometer and topography light sources, the coatings for reducing the diffused light effects are to be adapted accordingly.

Figure 3:
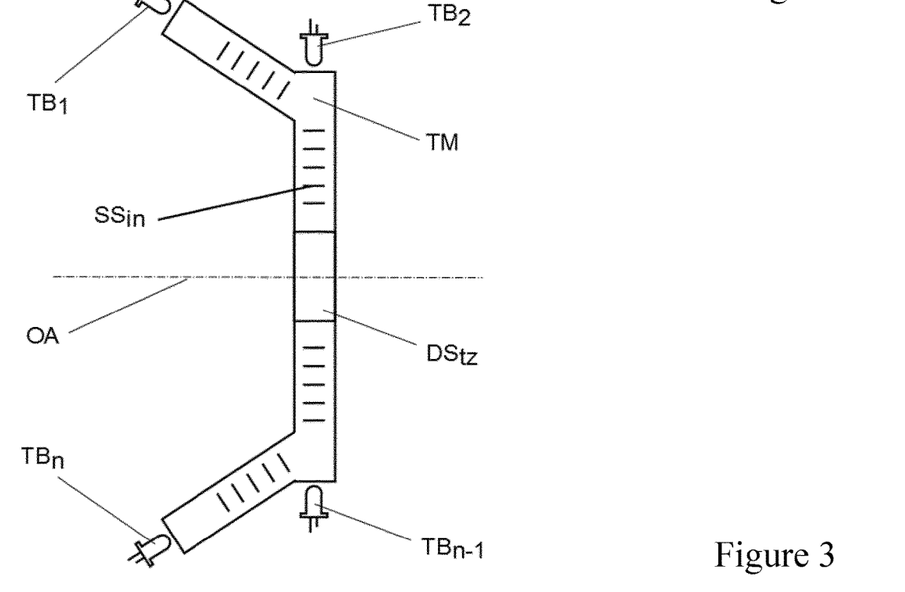
FIG. 3: depicts a cross section of a topography module having an expanded measurement range.

FIG. 3 depicts a topography module having an expanded measurement region, in a cross sectional view. The topography module TM here also has diffusing inhomogeneities $SS_{in}$ in the interior of the disk volume, for the illumination of which, a number n of topography light sources TB are disposed on the topography module TM, which represent the lighting unit as a whole.

The central region of the topography module TM, which has a coplanar form herein, contains both the telecentric detection beam path $DS_{tz}$ as well as the region for the keratometry beams. As a result, a distortion of the keratometry beams can be prevented in the transmission, or at least minimized. A larger measurement region on the cornea can be covered by the conical region adjoining it at the periphery.

Figure 4:
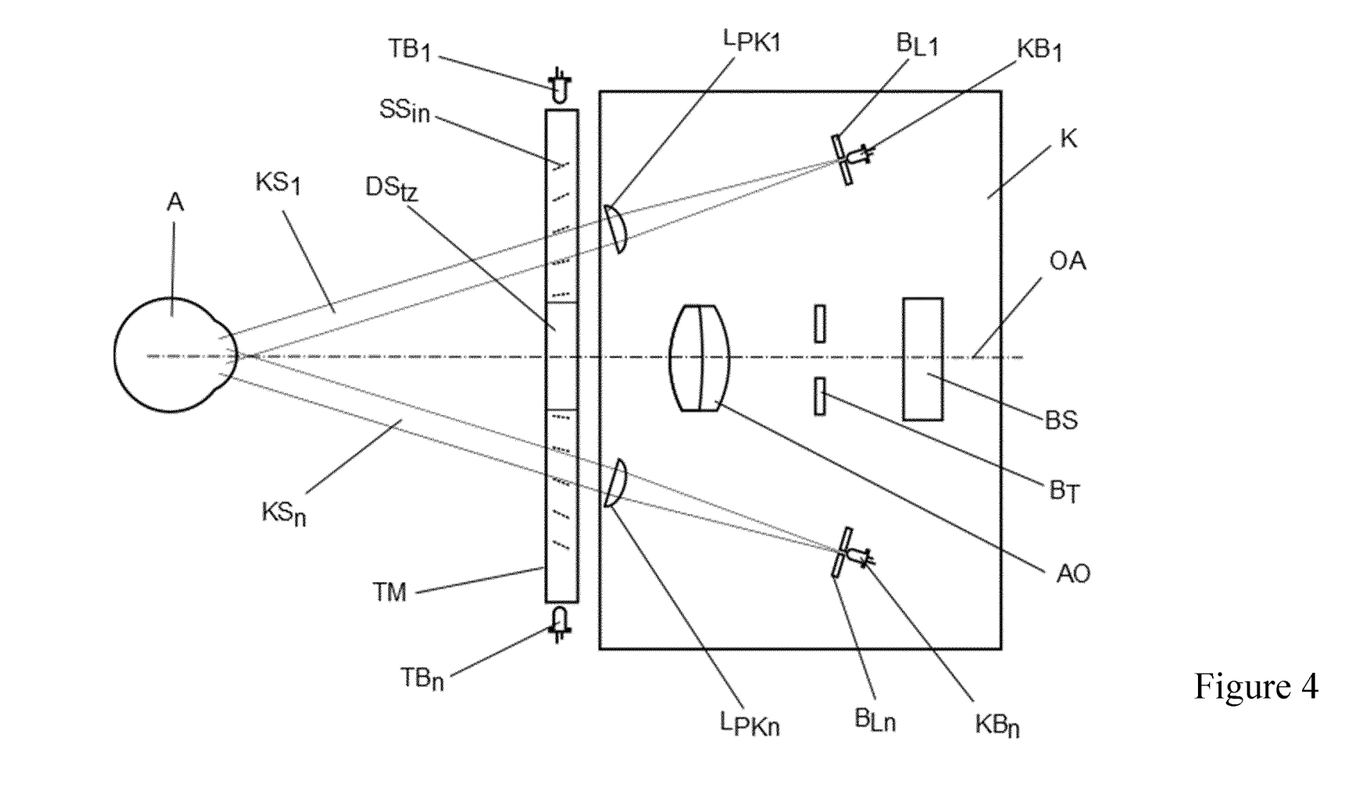
FIG. 4: depicts the fundamental construction of a 6 point keratometer with a topography module.

FIG. 4 shows the fundamental construction of a 6 point keratometer having the topography module according to the invention.

The 6 point keratometer K is composed thereby of the telecentric detection beam path $DS_{tz}$, having an imaging lens AO, a telecentric aperture $B_T$ and an image sensor BS, as well as the beam paths $KS_n$ for the keratometer light sources $KB_n$ having a pinhole aperture $B_{Ln}$ and a plano-convex lens $L_{PKn}$. The topography module TM, having the local diffusing inhomogeneities $SS_{in}$ and the topography light sources $TB_n$ is disposed between the eye A and the 6 point keratometer K, preferably directly in front of the 6 point keratometer.

It can be seen in FIG. 4 that the topography module TM has no local diffusing inhomogeneities $SS_{in}$ in either the region of the telecentric detection beam path $DS_{tz}$, or in the region of the beam paths $KS_n$ of the keratometry light sources $KB_n$, that could affect them.

The light sources $KB_n$ and $TB_n$ are preferably designed such that the emission of light occurs in the near infrared spectral range, in order to avoid interfering with the patient's ability to maintain a specific line of sight.

Because the keratometry structures are projected onto the eye from the infinite, in general they will have a slightly different focusing plane in the imaging on the camera chip than the topography structure. This is caused by the reflected imaging on the cornea surface (or on the precorneal tear film). This difference can be compensated for when the two emission wavelengths differ from one another in a defined manner. In this case, the focusing planes are displaced against one another through the chromatic aberration of the imaging lens, and via an appropriate alignment of the two light source wavelengths and the imaging lens, the desired result can be obtained.

It is particularly preferred therefore that the emission wavelengths are selected such that at an optimal measurement distance, both the keratometer as well as the topography structures are sharply focused on the camera sensor.

In another design, the topography module is not transparent, wherein there are two variations for this.

If the non-transparent topography module is to remain in the beam path, then corresponding openings are to be provided for the keratometer light sources, a potentially existing slit lamp, and the detection beam path. This results, however, in a reduction in the amount of available data.

These openings are not necessary if the non-transparent topography module is subsequently inserted in the beam path, i.e. only for the topography measurement. This is possible using a fold-down or sliding mechanism. The consequences of this, however, are that the sequential measurements require substantially more time.

In this variation it is even conceivable that the topography module is mechanically entirely separate, and can be attached to the ophthalmological device by means of magnets, for example. It should be noted, however, that a precisely reproducible positioning of the topography module in the measurement position is necessary, which can be ensured by means of appropriate stops or snap-in devices.

Embodiments for non-transparent add-on modules of this type are well known to the person skilled in the art, from diverse commercial devices and patent applications, such that these are only mentioned here for the sake of completeness.

For an exact determination of the topography of the cornea of an eye by use of individual light structures or Placido ring systems, it is absolutely necessary, due to the type of light source, to know or determine the distance between the eye, or cornea, respectively, and the measurement device.

Figure 5:
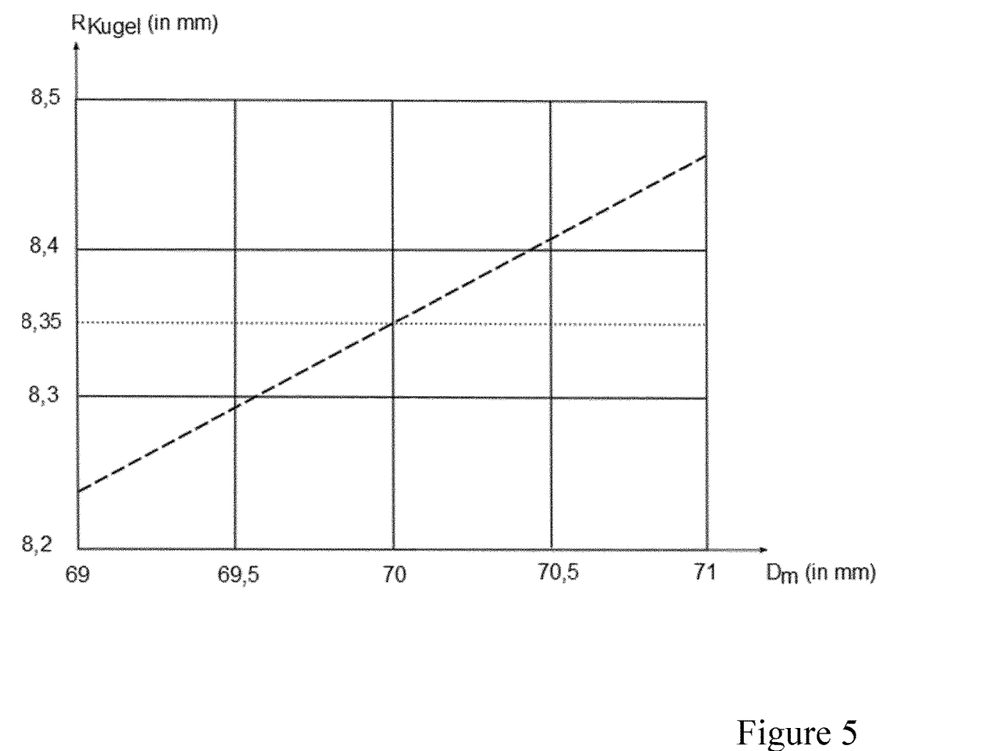
FIG. 5: is a graph illustrating the dependency of the determined radius on the actual distance between the eye and the measurement device.

For this, FIG. 5 shows the effect of the actual distance between the eye and the measurement device for determining the radius based on a spherical model. The correct radius $R_{Kugel}$ of 8.35 mm is established at a measurement distance $D_m$ of 70 mm between the eye and the measurement device. With a deviation in the measurement distance $D_m$ of only 0.5 mm, the established radius $R_{Kugel}$ already deviates by more than 0.06 mm from the correct radius $R_{Kugel}$.

With the disclosed method, it is not necessary to determine the actual distance between the eye and the measurement device, because the established keratometric data are taken into account in the evaluation of the topographic data, and the distance is established indirectly thereby.

The method according to example embodiments of the invention for the keratometric and topographic measurement of the cornea of an eye using a topography module for ophthalmological devices, in which the keratometric measurement of the eye is illuminated and detected in a distance-independent manner, and in which the topography module is positioned in the beam path in a first step, and is integrated into the control and evaluation logarithm, is characterized by the following steps:
  b) recording of a second image, in which the fixation light and the light sources for the keratometric measurement are switched on,
  c) recording of a third image, in which the fixation light and the light sources for the topographic measurement are switched on,
  e) evaluation of the recorded images and outputting the results.

The keratometric and topographic measurement of the cornea of an eye in the proposed method can be improved even more by the following steps:
  a) recording of a first image, in which only the fixation light is switched on, and
  d) recording of a fourth image, in which the fixation light and an infrared lamp are switched on.

In step a), the reflections striking the cornea from the surroundings are recorded under measurement conditions, i.e. when the eye is directed at the fixation light, in order to be able to eliminate them from the recordings in the evaluation. In contrast, the recordings made in step d) help in distinguishing the edge of the iris from the annular structures of the keratometer light sources.

The measurement sequence for keratometry and topography for example occurs such that numerous recording cycles are carried out with this set sequence. In this case, the keratometry and topography measurements are to be regarded as simultaneous, and it is thus avoided that possible deviations need to be taken into account in calculating the consistency of the measurement data.

In order to accelerate the method, steps b) and c) can be carried out simultaneously.

In accordance with the invention, the steps a) to d) are repeated numerous times, in order to obtain the greatest possible consistency between the topographic data and the keratometric data, and to output this as the result. In order to determine the greatest possible consistency thereby, the curvature radii at the keratometric measurement points are compared with the curvature radii at these measurement points, established on the basis of the topographic data, and varied if necessary.

The comparison, or a necessary variation, respectively, occurs thereby based on the images recorded in steps a) to c), as follows.

The curvature radius $R_K$ of the cornea is absolutely precisely determined from the (keratometric) image recorded in step b). The topography of the cornea can be determined from the image recorded in step c), although its simulated curvature radius $R_T$ may not be correct, because the distance between the cornea and the measurement device is unknown.

The curvature radii $R_K$ and $R_T$ are then compared. If both curvature radii are identical, or the deviation lies within an acceptable tolerance, then the results can be output in step e). Otherwise, in the evaluation of the topography data, they are varied until the curvature radii $R_K$ and $R_T$ are identical, or their deviation lies within an acceptable tolerance.

Figure 6:
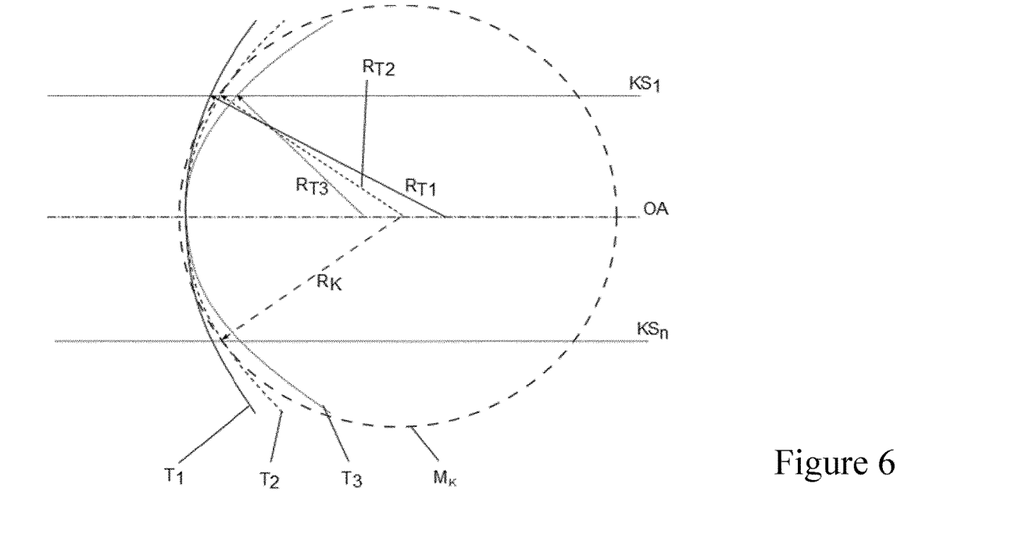
FIG. 6: is the schematic depiction of three variations of a scaled topography.

For this, FIG. 6 shows a schematic depiction of three variations of a varied topography $T_1$, $T_2$, $T_3$ with their curvature radii $R_{T1}$, $R_{T2}$, and $R_{T3}$, as well as the curvature radius $R_K$ determined from the keratometric imaging based on a spherical model $M_K$. It can be derived from FIG. 6 that the curvature radius $R_K$ most closely resembles the varied topography $T_2$ having the curvature radius $R_{T2}$.

The variation occurs thereby, such that the topography for various (but not known) distances between the cornea and the measurement device are determined from the recording made in step c).

The working distance, for example, for which diffusion structures are imaged in a normal eye at maximum sharpness on the image sensor, can be selected as the starting value.

The variation can occur, for example, in that the topography are scaled accordingly, directly at the points of the keratometer measurement, or on a surface function fitted to the topography. This can be achieved with both radii data as well as gradient data.

The evaluation of the images recorded with keratometric lighting according to step e) can be based thereby on a spherical model or a toric model.

Fundamentally, it is also possible to use the proposed topography module for ophthalmological devices that also have a distance measurement device or a distance setting device. In this case, the evaluation of the topography data can occur without direct reference to the keratometry data.

Here as well, however, the greatest possible consistency between the topographic data and the keratometric data is established, and this is output as the result. The necessarily present distance measurement device is used to indicate possible faulty measurements. If the deviations between the two measurement methods exceed an established tolerance, a warning message is issued. The measurement must then be repeated.

A solution is provided with the present invention, which makes it possible for ophthalmological devices that have a distance-independent keratometry measurement device, to also implement topographic measurements on an eye, and this being without knowing or having to determine the distance between the cornea and the measurement device.

The solution thus unites the advantages of keratometric and topographic measurements of an eye with limited technical expenditure. The present invention suitable both as an alternative add-on module, and also, with the appropriate adjustments, as a retrofitting module, for ophthalmological devices already in use. In particular, embodiments of the invention suitable for use in distance-independent 6 point keratometers.

The invention claimed is:

1. A topography module for ophthalmological devices that have a distance-independent keratometry measurement device having a detection beam path including including elements for distance independent keratometry measurement, elements for illumination and detection, as well as elements for control and evaluation, wherein:
   the topography module generates a luminous pattern, and
   the topography module is disposed, in a stationary or moveable manner, in a beam path between the ophthalmological device and the eye,
   wherein the topography module transmits a keratometry beam, and
   includes devices that facilitate placement of the topography module at a definite position in the beam path between the ophthalmological device and the eye,
   wherein an existing control unit of the ophthalmological device is adapted for controlling the topography module appropriately for generating light patterns,
   wherein an existing evaluation unit is suitable for evaluating the reflected images of an eye recorded and transmitted by the detection unit in both a keratometric as well as topographic manner; and
   wherein the topography module is transparent, and for generation of the light pattern necessary for topography measurements, has local light decoupling inhomogeneities in a volume thereof or structures on its surface, or an opto-electronic coating.

2. The topography module according to claim 1, wherein the detection beam path of the distance-independent keratometry measurement device is telecentric.

3. The topography module according to claim 1, wherein the topography module has a disk-shaped, planar, conical or similar form.

4. The topography module according to claim 1, further comprising rings, grids, points, bars that are used as the light pattern for topography measurements.

5. The topography module according to claim 1, further comprising a lighting unit that is disposed, for illumination of the local light decoupling inhomogeneities in its volume, or the structures on its surface, such that light is laterally introduced into a peripheral surface or surfaces of the topography module.

6. The topography module according to claim 5, wherein the lighting unit is composed of numerous light sources distributed over the circumference.

7. The topography module according to claim 1, wherein the local diffusing inhomogeneities in the volume thereof, or the structures in or on the surface thereof are disposed such that both the beams of the keratometer light sources as well as the telecentric detection beam path are not affected.

8. The topography module according to claim 1, further comprising a coating in the form of an OLED film that is used as the opto-electronic coating for generating the light pattern for topography measurements.

9. The topography module according to claim 8, wherein the OLED film is capable of depicting luminous light patterns through an appropriate activation by the control unit, such that there is no need for a lighting unit.

10. The topography module according to claim 9, wherein arbitrary dynamic light patterns can be depicted with the OLED film, depending on activation thereof, and wherein the light patterns can be varied in terms of color and contrast.

11. The topography module according to claim 9, wherein, in addition to the light patterns necessary for the topography measurement, additional light points for fixation can be depicted with the OLED film, depending on the activation thereof.

12. The topography module according to claim 1, further comprising appropriate coatings and/or covers for reducing effects of diffused light.

13. A method for keratometric and topographic measurement of a cornea of an eye using a topography module for ophthalmological devices, comprising:
   illuminating and detecting the eye distance-independently for a keratometric measurement, and positioning the topography module in a beam path;
   integrating the topography module into a control and evaluation logarithm of the ophthalmological devices;
   b) recording a second image, in which a fixation light and a light sources for the keratometric measurement are switched on,
   c) recording a third image, in which the fixation light and the light sources for the topographic measurement are switched on, and
   e) evaluating the recorded images, and outputting the results
   wherein, to determine the greatest possible consistency, first curvature radii at keratometric measurement points are compared with the second curvature radii determined based on the topographic data, at the keratometry measurement points and wherein the topographic data can be varied if necessary.

14. The method according to claim 13, further comprising:
   f) recording a first image, in which only the fixation light is switched on,
   g) recording a fourth image, in which the fixation light and an infrared lamp are switched on.

15. The method according to claim 14, wherein the steps a) to d) can be repeated numerous times, to obtain a greatest possible consistency between the topographic data and the keratometric data, and outputting a result thereof.

16. The method according to claim 13, wherein the steps b) and c) can be executed simultaneously.

17. The method according to claim 13, wherein the topographies are determined for different distances between the cornea and measurement device in order to vary the recording or recordings made in step c).

18. The method according to claim 13, wherein evaluation of the images recorded with keratometric lighting in step e) are based on a spherical model.

19. The method according to claim 13, wherein evaluation of the images recorded with topographic lighting in step e) are based on a toric model.

* * * * *

UNITED STATES PATENT AND TRADEMARK OFFICE
CERTIFICATE OF CORRECTION

PATENT NO. : 10,213,103 B2
APPLICATION NO. : 15/315319
DATED : February 26, 2019
INVENTOR(S) : Reich et al.

Page 1 of 1

It is certified that error appears in the above-identified patent and that said Letters Patent is hereby corrected as shown below:

In the Claims

Column 10, Line 16, delete the second occurrence of "including".

Signed and Sealed this
Third Day of September, 2019

Andrei Iancu
*Director of the United States Patent and Trademark Office*